United States Patent [19]
Levitzki et al.

[11] Patent Number: 5,932,580
[45] Date of Patent: Aug. 3, 1999

[54] PDGF RECEPTOR KINASE INHIBITORY COMPOUNDS THEIR PREPARATION AND COMPOSITIONS

[75] Inventors: Alexander Levitzki; Aviv Gazit; Shmuel Banai; S. David Gertz, all of Jerusalem; Gershon Golomb, Efrat, all of Israel

[73] Assignee: Yissum Research and Development Company of the Hebrew University of Jerusalem, Jerusalem, Israel

[21] Appl. No.: 08/980,596

[22] Filed: Dec. 1, 1997

[51] Int. Cl.$^6$ .......... A01N 43/58; C07D 241/36; C07D 471/00
[52] U.S. Cl. .......... 514/249; 514/250; 544/344; 544/345; 544/353
[58] Field of Search .................. 514/249, 250; 544/344, 345, 353

[56] References Cited

U.S. PATENT DOCUMENTS

| | | | |
|---|---|---|---|
| 4,954,498 | 9/1990 | Mertens et al. | 514/254 |
| 5,116,843 | 5/1992 | Mertens et al. | 514/253 |
| 5,480,883 | 1/1996 | Spada et al. | 514/249 |
| 5,712,395 | 1/1998 | App et al. | 544/344 |
| 5,763,441 | 6/1998 | App et al. | 514/249 |

FOREIGN PATENT DOCUMENTS

WO 92/20642  11/1992  WIPO .

OTHER PUBLICATIONS

Gazit et. al., "Tyrphostins. 5. Potent inhibitors . . . ", J. Med. Chem., vol. 39, pp. 2170–2177, 1996.

Kovalenko et. al., "Selective Platelet–Derived Growth Factor . . . ", Cancer Res., vol. 54(23), pp. 6106–6114, Dec. 1, 1994.

*Primary Examiner*—Mukund J. Shah
*Assistant Examiner*—Tamthom N. Truong
*Attorney, Agent, or Firm*—Mark M. Friedman

[57] ABSTRACT

PDGF receptor kinase inhibitory compounds of the quinoxaline family, methods for their synthesis and containment is slow release pharmaceutical preparations, and their use for treatment of proliferative malignant and non-malignant diseases or disorders by local or systemic application. A compound according to the invention includes a tyrphostin of the general formula:

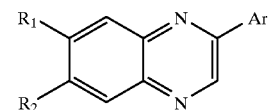

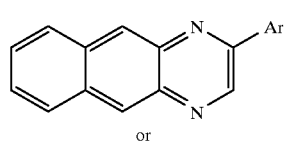

or

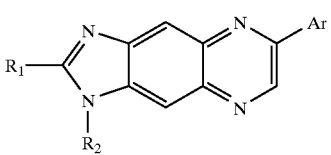

wherein R1 and R2 are each independently selected from the group consisting of alkyl, alkoxy, halogen, nitro and amine and Ar is selected from the group consisting of phenyl, ferrocene, thiophene, furane, pyrrole, indole, thiazole, imidazole and pyridine.

15 Claims, 9 Drawing Sheets

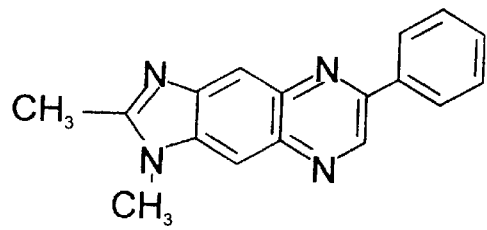 AG 1851
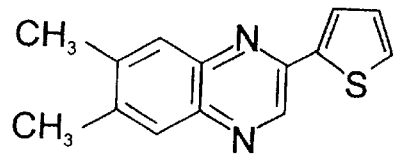 AG 1990
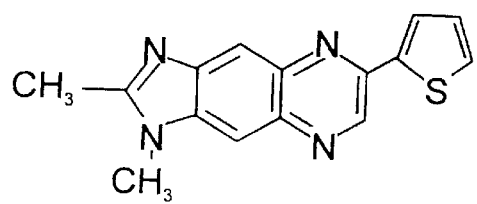 AG 1992
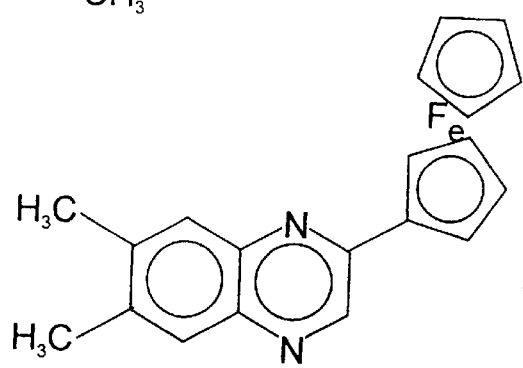 AG 1989
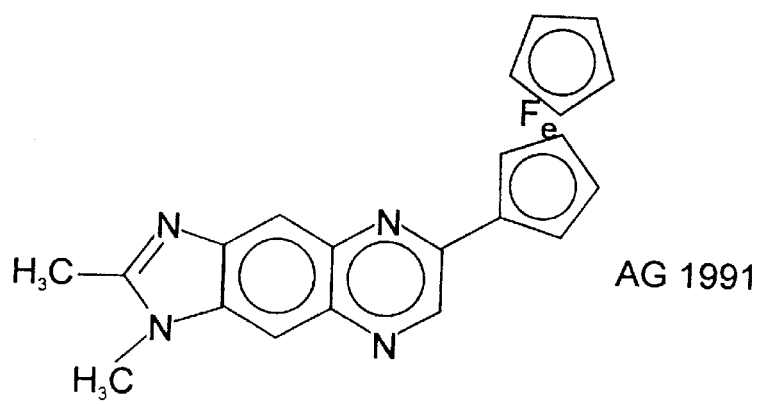 AG 1991
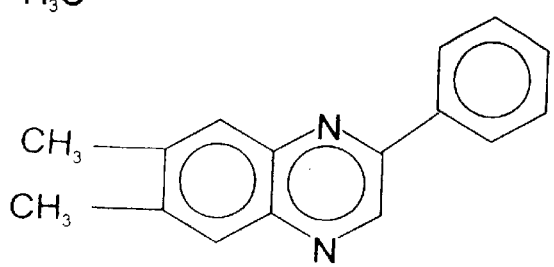 AG 1295
Fig. 1

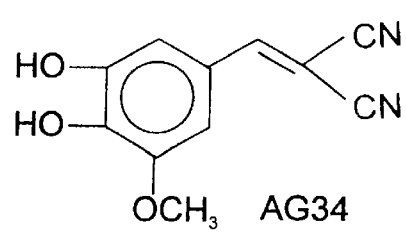 AG34
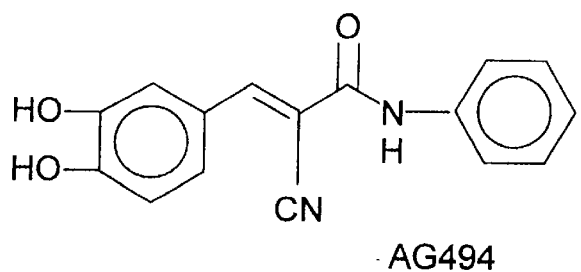 AG494
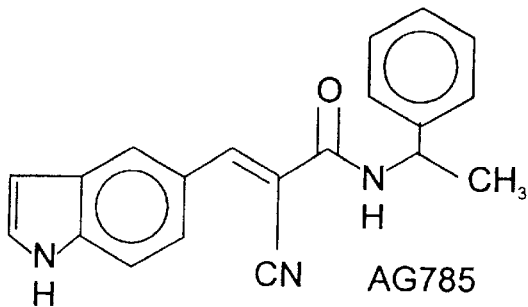 AG785
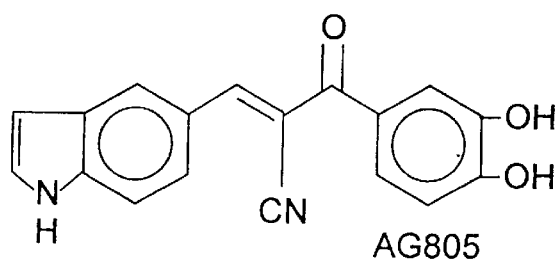 AG805
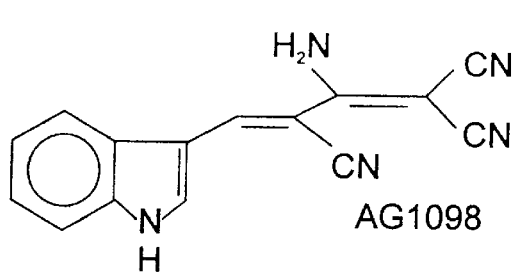 AG1098
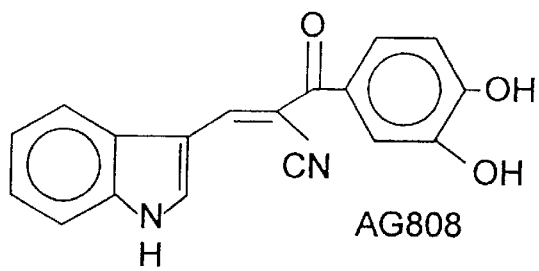 AG808
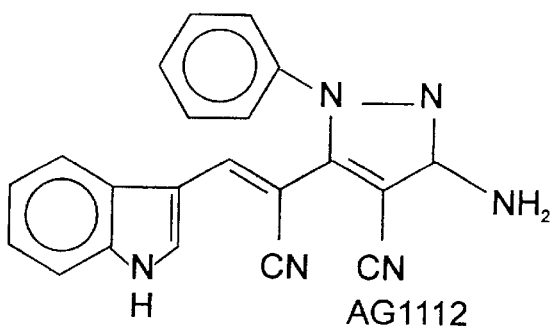 AG1112
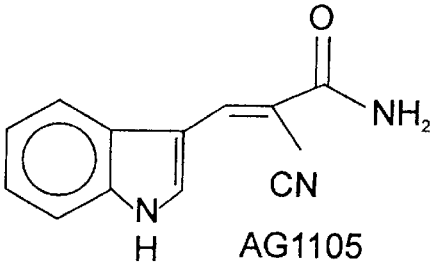 AG1105
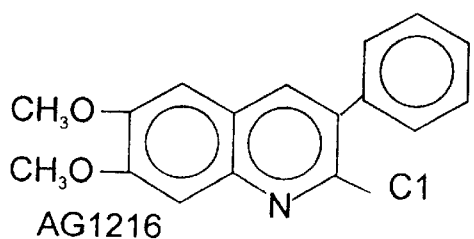 AG1216
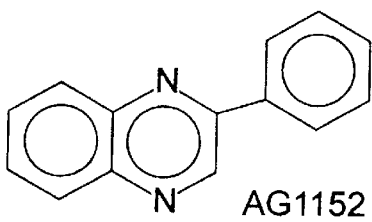 AG1152
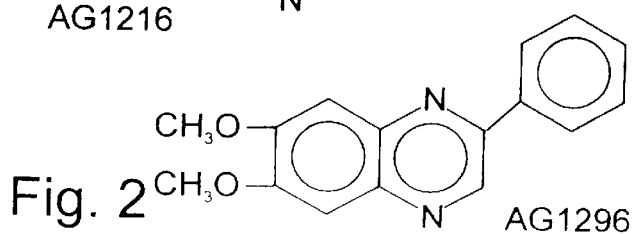 AG1296
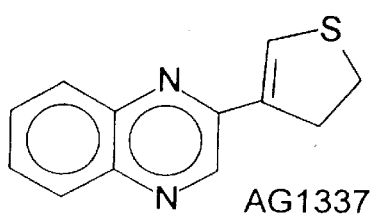 AG1337
Fig. 2

1

PDGF RECEPTOR KINASE INHIBITORY COMPOUNDS THEIR PREPARATION AND COMPOSITIONS

FIELD AND BACKGROUND OF THE INVENTION

The present invention relates to PDGF receptor kinase inhibitory compounds and compositions such as, but not limited to, slow release compositions. More particularly, the present invention relates to novel compounds and compositions of the quinoxaline family which are potent PDGF receptor kinase inhibitors, their synthesis, and their use for treatment of proliferative malignant and non-malignant diseases or disorders, such as, but not limited to, atherosclerosis, restenosis, vascular graft restinosis, instent stenosis, pulmonary fibrosis, glomerular nephritis, rheumatoid arthritis and PDGF receptor associated malignancies, such as, but not limited to, leukemias and limphomas.

Platelet derived growth factor (PDGF) is a potent mitogen for mesenchymal, glial, and capillary endothelial cells (for reviews, see, [1] and [2]). The three isoforms of PDGF, PDGF-AA, PDGF-AB, and PDGF-BB, interact differentially with structurally related receptors designated PDGF α- and β-receptors. Each of these receptors has an extracellular part featuring five immunoglobulin-like domains and an intracellular part with a tyrosine kinase domain containing a characteristic insert amino acid sequence [3–5]. The tyrosine kinase activity of these receptors is essential for transmission of the mitogenic signal into the cell [6].

PDGF and its receptors participate in various physiological processes such as embryonal development and wound healing. An abnormally high activity of PDGF is believed to play a central role in the etiology of certain adverse patho-physiological situations, such as atherosclerosis and restenosis [7,8], as well as in other non-malignant diseases such as pulmonary fibrosis [9], glomerular nephritis [10], and rheumatoid arthritis [11]. Moreover, the PDGF β-chain was acquired as the sis oncogene by the acutely transforming simmian sarcoma virus [12, 13]. The expression of a PDGF-like growth factor in cells infected with simian sarcoma virus or transfected with the sis oncogene leads to their transformation due to the persistent (lutocrine stimulation of the resident PDGF receptors.

Furthermore, certain human tumors possess PDGF receptors and express the genes for PDGF which suggests that autocrine growth stimulation via PDGF receptors contributes to the malignant phenotype of these tumors [2,14].

The fact that PDGF is likely to be involved in the development of certain disorders has prompted the search for agents to block the action of PDGF. The approaches for interference with PDGF-induced signalling include peptides competing with PDGF for receptor binding [15], dominant negative mutants of PDGF [16, 17] or of PDGF receptor [18], and low molecular weight blockers of the receptor tyrosine kinase activity known as tyrphostins [19].

Certain tyrphostins which block PDGF-dependent proliferation of rabbit vascular smooth muscle cells [20] and of human bone marrow fibroblasts [21] have already been reported.

A novel class of tyrosine kinase blockers represented by the tyrphostins AG1295 and AG1296 was described by Kovalenko et al. [22]. These compounds inhibit selectively the platelet-derived growth factor (PDGF) receptor kinase and the PDGF dependent DNA synthesis in Swiss 3T3 cells and in porcine aorta endothelial cells (EC) with 50% inhibitory concentrations below 5 and 1 μM, respectively. These PDGF receptor blockers have no effect on epidermal growth factor receptor autophosphorylation, weak effects on DNA synthesis stimulated by insulin, by epidermal growth factor, or by a combination of both and over an order of magnitude weaker blocking effect on fibroblast growth factor-dependent DNA synthesis.

AG1296 potently inhibits signalling of human PDGF α- and β-receptors as well as of the related stem cell factor receptor (c-Kit) but has no effect on autophosphorylation of the vascular endothelial growth factor receptor KDR or on DNA synthesis induced by vascular endothelial growth factor in porcine aortic endothelial cells. Treatment by AG1296 reverses the transformed phenotype of sis-transfected NIH 3T3 cells but has no effect on src-transformed NIH 3T3 cells or on the activity of the kinase p60c-src(F527) immunoprecipitated from these cells [22].

The present invention describe novel and potent tyrphostin compounds which possess an quinoxaline moiety, which show high selectivity towards the PDGF receptor kinase. These compounds are new leads for drugs which could potentially combat malignant as well as non-malignant proliferative disorders in which PDGF plays a prominent role.

SUMMARY OF THE INVENTION

According to the present invention there are provided PDGF receptor kinase inhibitory compounds of the quinoxaline family, methods for their synthesis and containment is slow release pharmaceutical compositions, and their use for treatment of proliferative malignant and non-malignant disorders by local or systemic application.

According to further features in preferred embodiments of the invention described below, provided is a compound comprising a tyrphostin of the general formula:

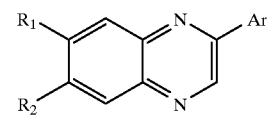

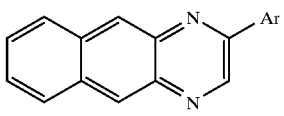

or

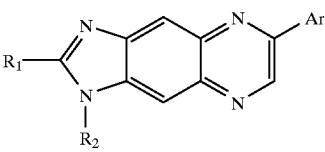

According to still further features in the described preferred embodiments R1 and R2 are each independently selected from the group consisting of alkyl, alkoxy, halogen, nitro and amine and Ar is selected from the group consisting of phenyl, ferrocene, thiophene, furane, pyrrole, indole, thiazole, imidazole and pyridine.

According to still further features in the described preferred embodiments the tyrphostin is AG1851, AG1989, AG1990, AG1991 or AG1992 (FIG. 1).

According to further features in preferred embodiments of the invention described below, provided is a pharmaceutical composition for slow release of tyrphostins comprising particles including a slow release carrier (typically, a polymeric carrier) and a tyrphostin compound.

According to still further features in the described preferred embodiments the slow release carrier is poly lactic acid.

According to still further features in the described preferred embodiments the tyrphostin compound is of the general formula:

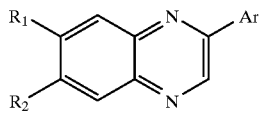

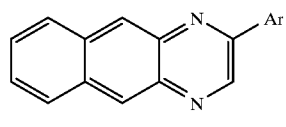

or

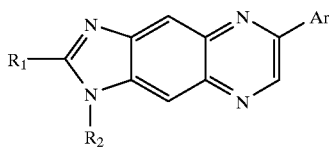

According to still further features in the described preferred embodiments R1 and R2 are each independently selected from the group consisting of alkyl, alkoxy, halogen, nitro and amine group and Ar is selected from the group consisting of phenyl, ferrocene, thiophene, furane, pyrrole, indole, thiazole, imidazole and pyridine.

According to still further features in the described preferred embodiments the tyrphostin compound is selected from the group consisting of AG1851, AG1990, AG1992, AG1989, AG1991, AG34, AG494, AG785, AG805, AG1098, AG808, AG112, AG1105, AG1216, AG1152, AG1296, AG1337 and AG1295 (FIGS. 1 and 2).

According to further features in preferred embodiments of the invention described below, provided is a method of inhibiting cell proliferation comprising the step of subjecting the cells to a tyrphostin compound selected from the group consisting of AG1851, AG1989, AG1990, AG1991 and AG1992 (FIG. 1).

According to further features in preferred embodiments of the invention described below, provided is a method of inhibiting cell proliferation comprising the step of subjecting the cells to a tyrphostin compound of the general formula:

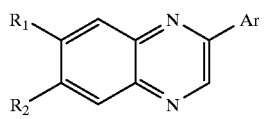

or

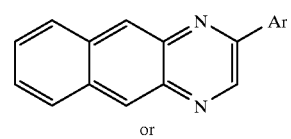

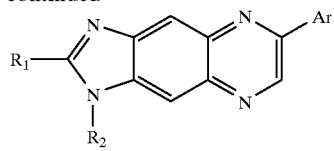

According to still further features in the described preferred embodiments the cells are of an organism, subjecting the cells to the tyrphostin compound is effected in vivo.

According to still further features in the described preferred embodiments subjecting the cells to the tyrphostin compound is effected in vitro.

According to further features in preferred embodiments of the invention described below, provided is a method of treating a proliferative disorder of an organism, comprising the step of applying to the organism a pharmaceutical composition which includes particles including a slow release carrier (typically, a polimeric carrier) and a tyrphostin compound.

According to further features in preferred embodiments of the invention described below, provided is a method of locally treating a proliferative disorder of a tissue of an organism comprising the step of locally applying to the tissue a pharmaceutical composition which includes particles including a slow release carrier and a tyrphostin compound.

According to still further features in the described preferred embodiments the organism is a human being.

According to still further features in the described preferred embodiments the tissue is an artery.

According to still further features in the described preferred embodiments the proliferative disorder is selected from the group consisting of psoriasis, papilloma, restenosis, atherosclerosis, in-stent stenosis, vascular graft restinosis, pulmonary fibrosis, glomerular nephritis, rheumatoid arthritis and PDGF receptor associated malignancies.

According to further features in preferred embodiments of the invention described below, provided is a method of preparing a pharmaceutical composition for slow release of tyrphostins comprising the steps of (a) dissolving or dispersing a slow release carrier (typically, a polimeric carrier) and a tyrphostin compound in an organic solvent for obtaining an organic solution containing the carrier and the tyrphostin compound; (b) adding the organic solution into an aqueous solution for obtaining an oil-in-water-type emulsion; and (c) evaporating the organic solvent from the oil-in-water-type emulsion for obtaining a colloidal suspension of particles containing the slow release carrier and the tyrphostin.

According to still further features in the described preferred embodiments the slow release carrier is poly lactic acid.

According to still further features in the described preferred embodiments the tyrphostin compound is any one or combination of the compounds described above.

According to still further features in the described preferred embodiments the organic solvent includes acetone and dichloromethane.

According to still further features in the described preferred embodiments the aqueous solution includes Poloxamer F68.

The present invention successfully addresses the shortcomings of the presently known configurations by providing new and potent tyrphostins and delivert system for treatment of proliferative disorders.

BRIEF DESCRIPTION OF THE DRAWINGS

The invention herein described, by way of example only, with reference to the accompanying drawings, wherein:

FIGS. 1 and 2 present chemical formula of tyrphostin compounds according to the present invention;

DESCRIPTION OF THE PREFERRED EMBODIMENTS

Figure 3:
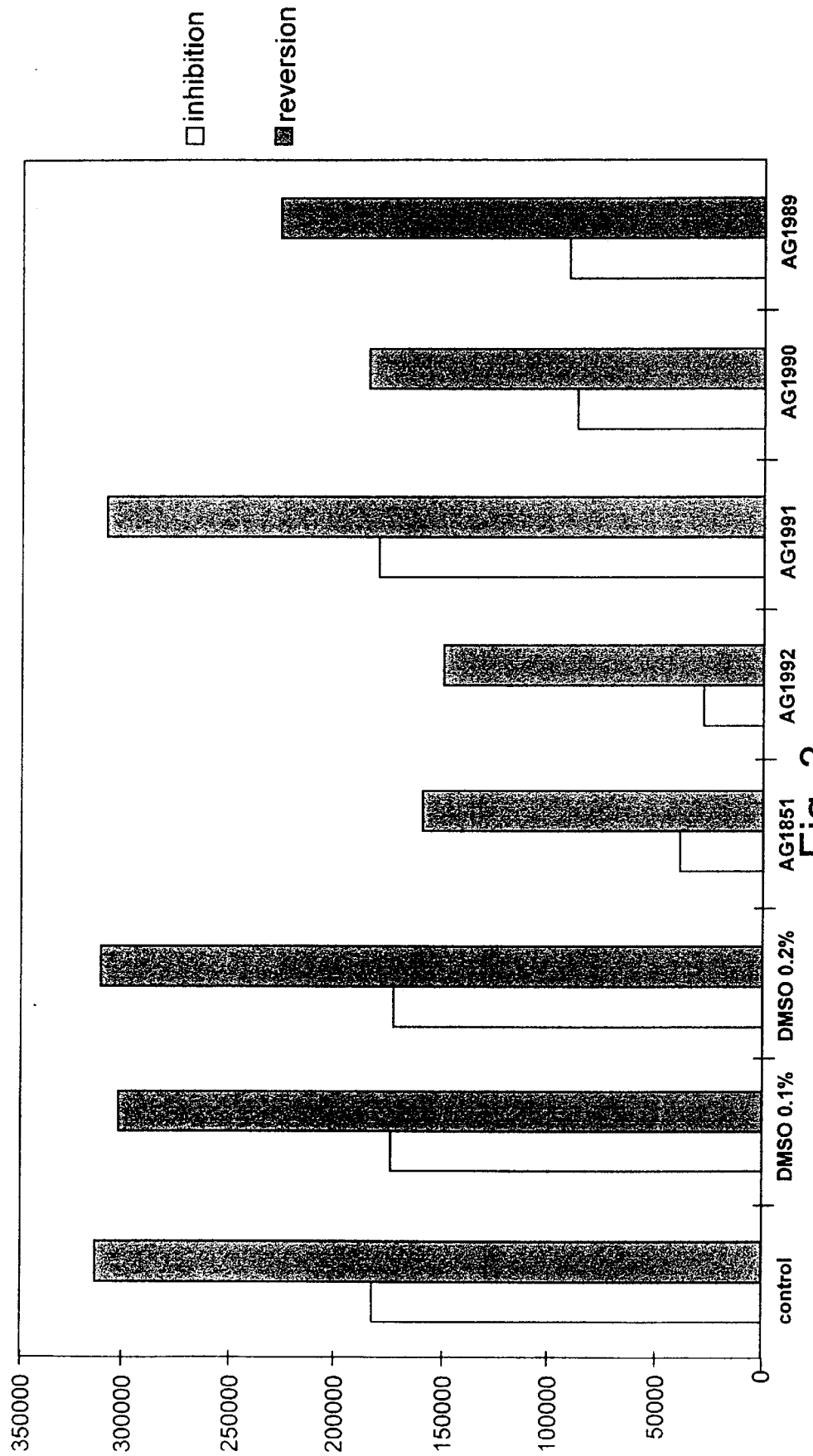
FIG. 3 is a bar graph presenting the maximal inhibitory and recovery effects of tyrphostins on porcine arterial smooth muscle cell (SMC) growth.

The present invention is of PDGF receptor kinase inhibitory compounds of the quinoxaline family, their synthesis and containment is slow release pharmaceutical compositions, and their use for treatment of proliferative malignant and non-malignant disorders, such as, but not limited to, atherosclerosis, restenosis, pulmonary fibrosis, in-stent stenosis, vascular graft restinosis, glomerular nephritis, rheumatoid arthritis and PDGF receptor associated malignancies by local or systemic application.

Proliferation and migration of activated smooth muscle cells (SMC), associated with release of abundant extracellular matrix by these cells, are fundamental to neointimal growth associated with accelerated arteriosclerosis which continues to plague patients undergoing balloon angioplasty, stent deployment, coronary artery bypass surgery, and heart transplantation.

Injury to the vessel wall, with or without loss or damage to the endothelium, causes a subpopulation of the quiescent differentiated SMC to lose their contractile myofilamentary apparatus and transform into synthetic cells with large amounts of rough endoplasmic reticulum, ribosomes, and mitochondria. This transformation, directed, at least partially, by PDGF, is associated with SMC migration and proliferation followed by elaboration of abundant extracellular matrix. A variety of experimental studies have been directed toward the attenuation of SMC in vitro and in vivo. Nonetheless, relatively little progress has been made in the development of effective, selective, non-toxic inhibitors of SMC growth which might eventually be applied in the interventional setting. Recent progress in determining the mechanisms by which growth factors control cell proliferation has contributed to the development of treatment strategies which target specific signal transduction pathways in order to control proliferative disorders. The binding of specific growth factors with their selective cell surface receptor tyrosine kinases results in its autophosphorylation and activation leading to downstream signal transduction through chains of intercommunicating proteins culminating in cell proliferation.

Inhibitors of protein tyrosine kinases (PTKs) have been shown to suppress SMC chemotaxis and proliferation. The tyrphostin phosphorylation inhibitors, are low molecular weight, synthetic compounds whose basic structure can be modified to block specific receptor PTKs or intracellular PTKs. Unlike larger receptor antibodies, the small size of the tyrphostins permits easier access to receptor sites within tissues such as in the depths of the media.

Recent studies have suggested that the profound selective PTK inhibition of such compounds results from competitive or mixed competitive interaction with the ATP binding domain as well as mixed competitive inhibition with substrate binding sub-sites [23].

The development of this class of compounds was based on the concept that it would lead to a more focused control of proliferative disorders, achieve more improved therapeutic indices, and reduce the numerous untoward side effects of the more generalized inhibitors of DNA or RNA synthesis or cytoskeleton-disrupting agents. It was recently shown that controlled local delivery of the non-selective PTK blocker AG17 (RG50872) effectively inhibits neointimal formation in a rat carotid balloon injury model [24].

The signal transduction induced by PDGF-BB, considered by many to be the strongest known mitogen and chemoattractant for arterial SMC, stimulates directed migration and proliferation of arterial SMC into the neointima following arterial injury. Platelet derived growth factor (PDGF), expressed by platelets, SMC, endothelial cells, and macrophages, has been shown to play an important role in the pathogenesis of injury-induced neointimal formation in the arterial wall acting as both a mitogen and chemoattractant for SMC as well as being involved in the transformation of SMC from their contractile to the proliferative phenotype. In vivo studies have demonstrated that the expression of PDGF ligand and its receptor are elevated following arterial injury.

Infusion of PDGF into injured rat carotid arteries, or transfection of a plasmid coding for PDGF into porcine arteries, have also been shown to increase neointimal formation. PDGF receptor levels in SMC from human atherosclerotic plaques have also been reported to be elevated compared to receptor levels in normal medial SMC. Recently, Sirois et al. [25] have shown marked upregulation of PDGF receptors following injury to the vessel wall. They have demonstrated that the degree of neointimal formation substantially depends on both PDGFR-$\beta$ overexpression and its activation by PDGF-BB. They demonstrated further that controlled local delivery of antisense oligonucleotides to PDGF-$\beta$ receptor reduces neointimal formation in the rat carotid injury model.

Finally, PTK blockers of the tyrphostin family have been shown to block PDGF receptor signal transduction, including the phosphorylation and activation of PLC$\gamma$, believed to be involved in SMC migration [20, 21, 22, 26].

We, therefore, hypothesized that selective blockade of PDGF-$\beta$ receptor activation should also result in marked inhibition of SMC activation, migration and proliferation.

The experiments described below demonstrate that tyrphostin-mediated inhibition of the PDGF-$\beta$-receptor autophosphorylation results in the selective inhibition of SMC proliferation, in vitro, with a minimal inhibitory effect on endothelial cells. It is shown that the tyrphostins AG1295, AG1851, AG1990, AG1992 (see FIG. 1) completely inhibited the PDGF-BB induced phosphorylation of the PDGF β-receptor tyrosine residues of porcine arterial SMC without affecting the level of PDGF β-receptor protein present in these cells.

Thus, a compound according to the present invention is a tyrphostin of the general formula:

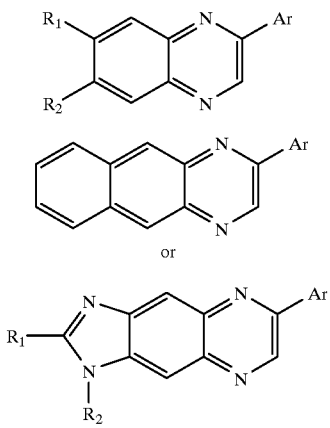

R1 and R2 are each independently, for example, alkyl, alkoxy, halogen, nitro and amine and Ar (i.e., Aryl group) is, for example, phenyl, ferrocene, thiophene, furane, pyrrole, indole, thiazole, imidazole and pyridine. According to a preferred embodiment of the present invention the compound is AG1851, AG1989, AG1990, AG1991 or AG1992, whose formulas are given in FIG. 1.

The chemical synthesis of these tyrphostins is typically governed by the following general protocols, wherein R1 and R2 are, for example, as defined above, or replaced by a benzoring:

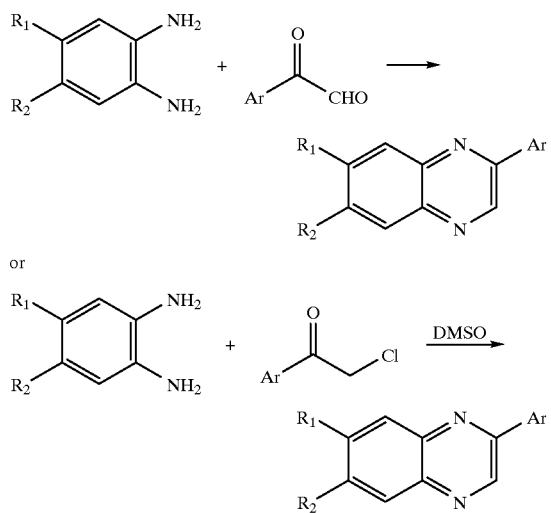

Further according to the present invention provided is a pharmaceutical composition for slow release of tyrphostins. The composition includes particles including a slow release carrier (typically, a polimeric carrier), such as, for example, poly lactic acid, and a tyrphostin compound. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/disolve in body fluids and release the active compound(s) therein. The particles are preferably nanoparticles (i.e., in the nanometer range, e.g., in the range of about 1 to about 500 nm in diameter, preferably about 50–200 nm in diameter, most preferably about 100 nm in diameter).

According to a preferred embodiment of the invention the tyrphostin compound is one of the above compounds or is one or more of the following: AG1851, AG1990, AG1992, AG1989, AG1991, AG34, AG494, AG785, AG805, AG1098, AG808, AG1112, AG1105, AG1216, AG1152, AG1296, AG1337 or AG1295, whose formulas are shown in FIGS. 1 and 2.

Any derivative of the above tyrphostins is also within the scope of the present invention.

Herein the term "derivative" refers to the result of a chemically altering, modifying or changing a molecule or a portion thereof, such that it still maintains its functionality.

Further according to the present invention provided is a method of inhibiting cell proliferation by subjecting the cells to a tyrphostin compound of the compounds hereinabove described. In a preferred embodiment the cells are of an organism (e.g., a human being), whereas subjecting the cells to the tyrphostin compound is effected in vivo. Alternatively, subjecting the cells to the tyrphostin compound is effected in vitro.

Further according to the present invention provided is a method of treating a proliferative disorder (disease) of an organism (e.g., a human being) by applying a slow release pharmaceutical composition as described above to the organism.

Hereinafter, the term "treat" includes substantially inhibiting, slowing or reversing the progression of a disease, substantially ameliorating clinical symptoms of a disease or substantially preventing the appearance of clinical symptoms of a disease.

Further according to the present invention provided is a method of locally treating a proliferative disorder of a tissue (e.g., an artery) of an organism applying a slow release pharmaceutical composition as described above onto the tissue. The proliferative disorder may be of any type associated with excessive or uncontrolled cell proliferation, including, but not limited to, psoriasis, papilloma, restenosis, atherosclerosis, in-stent stenosis, vascular graft restinosis, pulmonary fibrosis, glomerular nephritis, rheumatoid arthritis and PDGF receptor associated malignancies.

For therapeutic or prophylactic treatment, the compositions of tyrphostins of the present invention can be formulated in a pharmaceutical composition, which may include thickeners, carriers, buffers, diluents, surface active agents, preservatives, and the like, all as well known in the art. Pharmaceutical compositions may also include one or more active ingredients such as but not limited to anti inflammatory agents, anti microbial agents, anesthetics and the like in addition to tyrphostins.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, or intramuscular injection. Administration may also be done by implantation. In a preferred embodiment local application is by inshillation of a tyrphostin (or a composition containing the tyrphostin) from an angiopathy balloon, such that the tyrphostin is delivered to a balloon treated area of an artery.

Formulations for topical administration may include but are not limited to lotions, suspensions, ointments, gels, creams, suppositories, drops, liquids, sprays, emulsions and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions or suspensions which may also contain buffers diluents and other suitable additives.

Dosing is dependent on severity and responsiveness of the condition to be treated, but will normally be a single administration of a tyrphostin containing slow release composition, with course of treatment lasting from several days to several weeks or until a cure is effected or a diminution of disease state is achieved. Persons ordinarily skilled in the art can easily determine optimum dosages, dosing methodologies and repetition rates. In a preferred embodiment slow release application of the tyrphostins is effected as further described hereinabove and below.

Further according to the present invention provided is a method of preparing a pharmaceutical composition for slow release of tyrphostins.

The method includes the following steps.

First, a slow release carrier (typically, a polimeric carrier) and a tyrphostin compound are dissolved or disperssed in an organic solvent for obtaining an organic solution containing the carrier and the tyrphostin compound.

Second, the organic solution is added into an aqueous solution for obtaining an oil-in-water-type emulsion. Preferably, the aqueous solution includes surface active agent(s).

Third, the organic solvent is evaporated from the oil-in-water-type emulsion for obtaining a colloidal suspension of particles containing the slow release carrier and the tyrphostin.

The tyrphostin compound is, for example, any of the above mentioned tyrphostins. According to a prefered embodiment of the present invention the slow release carrier is poly lactic acid. The organic solvent preferably includes acetone and dichloromethane, whereas the aqueous solution preferably includes Poloxamer F68.

Reference is now made to the following examples, which together with the above descriptions, illustrate the invention in a non limiting fashion.

EXAMPLES

The following protocols and experimental details are referenced in the Examples that follow:

Chemical synthesis of tyrphostins and their analysis:

Synthesis of AG1851: 0.25 g, 1.4 mM, 1,2-dimethyl-5,6-diamino benzimidazole and 0.22 g, 1.44 mM, phenyl glyoxal in 15 ml ethanol were refluxed for 2 hours. Cooling, filtering and trituration with benzene-hexane gave 0.267 g (70% yield) of a brown solid, mp −288° C. NMR(CDCl$_3$): 9.30(1H,s), 8.44(1H,s), 8.22(2H,m), 7.94(1H,s), 7.50(3H, m), 3.88(3H,s), 2.74(3H,s). MS-274(M$^+$, 100%), 259(M-methyl, 7%), 247(M-HCN, 12%), 144(M-Ph-HCN-CN, 63%), 140(31%), 123(28%), m/e.

Synthesis of AG1990: 0.13 g, 0.9 mM, 4,5-dimethyl-1,2-diamino benzene and 0.15 g, 0.9 mM, chloroacetyl thiophene in 4 ml dimethyl sulfoxide (DMSO) were heated for 2 hours at 100° C. Water was added to the cooled solution and KOH was used to bring the acidic solution to neutral pH (7.0). Extraction with CH$_2$Cl$_2$ and chromatography gave 20 mg (10% yield) of a light yellow solid, mp −151° C. NMR(CDCl$_3$): 9.13(1H,s), 7.82(3H,m), 7.50(1H,m), 7.19 (1H,m), 2.49(6H,s). MS-240(M$^+$,100%), 225(M-methyl, 8%), 213(M-HCN, 6%), 198(M-methyl-HCN, 5%), 103 (14%) m/e.

Synthesis of AG1992: 0.07 g, 0.4 mM, 1,2-dimethyl-5,6-diamino-benzimidazole and 0.085 g, 0.52 mM, chloroacetyl thiophene in 4 ml DMSO were heated for 1.5 hours at 100° C. Water was added and the acidic solution was neutralized with KOH. Extraction with CH$_2$Cl$_2$ and chromatography gave, after trituration with benzene-hexane, 21 mg light brown solid, mp −125° C. NMR(CDCl$_3$) 9.23(1H, s), 8.36(1H,s), 7.86(2H,m), 7.50(1H,m), 7.20(1H,m), 3.87 (3H,s), 2.74(3H,s). MS-280(M$^+$,100%), 253(M-HCN, 12%), 144(M-thiophene-HCN-CN, 46%), 127(17%) m/e.

Synthesis of AG1989: 150 mg, 0.6 mM, 2-chloro benzoyl ferrocene and 80 mg, 0.6 mM, 4,5-dimethyl phenylene diamine and 4 ml DMSO were heated for 2 hours at 100° C. Workup (water, KOH followed by extraction with dichloromethane) and chromatography gave, after trituration with hexane, 10 mg, 5% yield, red solid. NMR(CDCl$_3$) 8.88(1H,s,H$_2$), 7.78.7.77(2H,2s), 5.09(2H,t,J=1.8 Hz), 4.53 (2H,t,J=1.8 Hz), 4.08(5H,s), 2.49.2.47(6H,2s), 2.71(3H,s).

Synthesis of AG1991: 130 mg, 0.5 mM, 2-chloro benzoyl ferrocene and 80 mg, 0.45 mM, 1,2-dimethyl 5,6-diamine benzimidazole and 4 ml DMSO were heated for 2 hours at 100° C. Workup (water, KOH followed by extraction with dichloromethane) gave, after trituration with hexane, 15 mg, 9% yield, red solid. NMR(CDCl$_3$) 8.96(1H,s), 8.30(1H,s), 7.86(1H,s), 5.13(2H,t,J=1.8 Hz), 4.55(2H,t,J=1.8 Hz), 4.11 (5H,s), 3.86(3H,s), 2.71(3H,s). MS-383(M$^+$,100%).

Synthesis of AG1295: The synthesis of AG1295 was as described in Kovalenko et al. [22].

The chemical formulas of these tyrphostins are shown in FIG. 1. The chemical formulas of additional tyrphostins which may be used according to the present invention are shown in FIG. 2.

Cell culture techniques and Assays:

Cells and reagents:

Smooth muscle cells (SMC) were obtained under aseptic conditions from porcine abdominal aortas, and human internal mammary arteries (IMA). Specimens from the operating room were transferred on ice to the tissue culture room. Each artery was cut open and the endothelial surface mechanically scraped. The vessels were then cut into 2 mm$^2$ fragments which were placed in culture dishes with Dulbecco's modified Eagle's medium (DMEM) supplemented with 15% (v/v) fetal calf serum (FCS), 100 u/ml penicillin, 100 μg/ml streptomycin, and 0.2M L-glutamine. The tissue fragments were then placed in an incubator at 37° C. under 9% CO$_2$ atmosphere until SMC outgrowth was detected (typically within 3–7 days). Uniform populations of SMC which displayed the characteristic "hill and valley" growth pattern were subcultured using 0.25% trypsin for transfer. For experiments testing the effect of tyrphostins on growth inhibition and recovery (see below), SMC from passages 1–3 were replated in 15 mm wells pretreated with 3 µg/cm² fibronectin (Biological Industries, Kibbutz Beit Haemek, Israel) at 15,000 cells/well.

Endothelial cells (EC) were isolated from porcine carotid arteries. Using aseptic procedure, both common carotid arteries were isolated, and the distal end of each artery was cannulated through an arteriotomy and ligated. The arteries were then perfused with phosphate buffered saline (PBS) and the proximal end ligated isolating a 5–7 cm long blood-free portion of the artery. The isolated portion of each artery was filled with PBS containing calcium and magnesium and 0.1% collagenase (Boehringer Manneheim, Germany). The segments were excised and incubated for 10 min at 37° C. in sterile bottles containing PBS. The arterial effluent was then flushed out with medium M-199 supplemented with 15% FCS, penicillin 100 u/ml, streptomycin 100 µg/ml, 0.2M L-glutamine, and 25 µg/ml endothelial cell growth substitute (ECGS, Biomedical technologies, Inc. Stoughton, Mass.) and collected in 50 ml centrifugation tubes containing 5 ml of the same medium. The cell suspension was centrifuged (200×g, 5 min) and the pellet resuspended in M-199 culture medium. Cells were seeded on fibronectin-coated dishes at a seeding density of 15,000 cells/well and incubated at 37° C. in 9% $CO_2$. ECGS (25 µg/ml) was added every other day until confluence was observed, typically within 6–8 days. At confluence, the cells were removed with trypsin-EDTA solution (0.25% Lrypsin and 0.05% EDTA in Puck's saline (Biological Industries, Kibbutz Beit Haemek, Israel), resuspended in the same culture medium, counted, and replated at 15,000 cells/well in fibronectin-coated 4-well dishes (15 mm) for growth inhibition experiments.

Swiss 3T3 cells (obtained from E. Rozengurt, London, United Kingdom) and NIH 3T3 cells, stably transfected with a constitutively active mutant (F527) of chicken c-src gene (generously provided by S. Courtneidge, Heidelberg, Germany), were grown in DMEM supplemented with 4 g/liter glucose, glutamic acid, antibiotics, and 10% FCS.

All cell culture reagents were from Gibco BRL, unless otherwise indicated. PDGF was the recombinant human BB homodimer. Murine EGF was kindly provided by E. Spitzer (Berlin, Germany). The anti-PDGF receptor antiserum DIG-1 was raised against a peptide corresponding to amino acid residues 1075–1089 in the human PDGF α-receptor but recognized PDGF α- and β-receptors equally well [22]. The antiserum PDGF-R3 against PDGF receptor [5] have been described. [γ-$^{32}$P]ATP were purchased from DuPont/N-EN (Dreieich, Germany). Additional reagents employed in specific experiments and their sources are indicated below.

Effect of tyrphostins on PDGF induced PDGFR autophosphorylation in intact SMC cells: Subconfluent porcine arterial smooth muscle cells, cultivated in Dulbecco's modified Eagle's medium (DMEM) supplemented with 15% fetal calf serum (FCS), were synchronized for 20 hours in a medium containing 2% FCS. Following preincubation with AG1295, AG1990, AG1991, AG1992, AG1851 or AG1989 (10 µM) for 60 min, and with $Na_3VO_4$ (100 µM) for 5 min, the cells were stimulated with PDGF-BB (100 ng/ml) for 10 min at 37° C. After stimulation, the cells were solubilized in Nonidet P-40 (1%) containing lysis buffer.

The analysis of PDGF p-receptor phosphorylation was performed as follows. Cell lysates were subjected to immunoprecipitation using the PDGF β-receptor specific antiserum R3 [5]. The percipitates were subjected to polyacrylamide (7.5%) gel electrophoresis in presence of sodium deducyl sulfate (SDS-PAGE) and were thereafter blotted onto a nitrocellulose membrane (Hybond C-EXTRA, Amersham). Phosphorylated proteins were detected by immunoblotting using the horseradish-peroxidase conjugated phosphotyrosine antibody RC20H (Transduction Laboratories), followed by chemoluminescence-based detection (ECL, Amersham) and autoradiography.

Detection of receptor proteins was performed as follows. Cell lysates were subjected to immunoprecipitation using the PDGF β-receptor specific antiserum R3 [5], as described above, and the percipitates washed three times and thereafter subjected to SDS-PAGE (7.5%) and blotting onto a nitrocellulose membrane (Hybond C-EXTRA, Amersham). Receptor proteins were detected by immunoblotting using the horseradish-peroxidase conjugated donkey anti-rabbit antibody (Amersham), followed by chemoluminescence-based detection (ECL, Amersham) and autoradiography.

Assay of receptor autophosphorylation in intact 3T3 cells: Confluent Swiss 3T3 cells in 24-well plates (Nunc) were incubated for 20–24 hours in serum-free DMEM. Subsequently, tyrphostins were added at concentrations ranging from 0 to 100 µM (final DMSO concentration, 0.5%) and the incubation was continued for 6–8 hours. The cells were then stimulated with 100 ng/ml PDGF-BB for 5 min at room temperature or 600 ng/ml EGF for 2.5 min on ice. The growth factor treatment was terminated by washing twice with ice-cold PBS and the cells were scraped off the wells in 60 µl lysis buffer containing 20 mM Hepes (pH 7.4), 150 mM NaCl, 1% Triton X-100, 10 mM sodium pyrophosphate, 50 mM NaF, 2 mM sodium-o-vanadate, 20 µm zinc acetate, 10 nM EDTA, 2 mM [ethylenebis (oxyethilenenitrilo)] tetraacetic acid, 1 mM phenylmethylsulfonyl fluoride, and 5 µg/ml leupeptin.

The cell lysates were clarified by centrifugation (cooled microfuge, 17,000 rpm, 15 min) and analyzed by SDS-PAGE (6.5% gels) and immunoblotting with anti-phosphotyrosine antibodies (either PY 20, ICN, and subsequently a peroxidase-coupled secondary antibody, or RC20-peroxidase conjugate, Affinity, Nottingham, United Kingdom). The blots were developed with a chemiluminescence detection system (Western Light, Tropix, or ECL, Amersham). In some experiments PDGF receptors were immunoprecipitated with PDGF-R3 or DIG-1 antibodies as described [25] prior to the analysis by immunoblotting with anti-phosphotyrosine antibodies.

Src kinase activity assay: src-transformed NIH 3T3 cells were grown in 24-well plates to confluency; rinsed twice with a solution containing 20 mM Tris, 0.1 mM sodium-o-vanadate, and 150 mM NaCl (pH 7.5); and lysed in 100 µl/well of lysis buffer containing 20 mM Tris (pH 8.0), 150 mM NaCl, 1% Nonidet P-40, 2.5 mM EDTA, 10 mM NaF, 1% trasylol, and 20 µm leupeptin. The lysate was clarified by centrifugation and subjected to immunoprecipitation with the anti-Src monoclonal antibody MAb 327 (Oncogene Science; 0.5 µg antibody/80 µg protein) for 1 hour at 4° C. Then, goat anti-mouse IgG (Sigma; 0.2 µg per 0.5 µg monoclonal antibody 327) was added and incubation was continued for 30 mi followed by another 40 min of incubation with 10 µl of protein A-Sepharose Cl-4B (Pharmacia). The immunoprecipitates were washed five times with the lysis buffer and twice with kinase buffer containing 40 mM Hepes (pH 7.4), 0.5 mM dithiothreitol, 5 mM $MnCl_2$, and 0.1 mM sodium-o-vanadate. The immunoprecipitates were suspended in kinase buffer and aliquots corresponding to 40 µg of cell lysate protein were preincubated with or without tyrphostin for 15 min at 30° C. Then, the kinase reaction was performed in the presence of 2 μg of acid-treated enolase and 10 μCi of [γ-$^{32}$P]ATP (2 μM) in a final volume of 30 μl. The reaction was terminated by addition of SDS-PAGE sample buffer (6% SDS, 30% β-mercaptoetlhanol, 40% glycerol, and 0.5 mg/ml bromophenol blue) and the incorporation of radioactivity in the enolase was analyzed by SDS-PAGE and autoradiography as well as Phosphor-Imager quantification.

Membrane autophosphorylation assays: Membranes were prepared from confluent cultures of Swiss 3T3 cells as described [22]. For measuring receptor autophosphorylation, 10 μg membrane protein per assay were incubated for 20 min on ice in the presence of 1.2 μg/ml EGF or 2 μg/ml PDGF, or both; 50 mM Hepes (pH 7.5); and 3 mm MnCl$_2$ (final concentrations) in a volume of 45 μl. In order to test the effects and determine the IC$_{50}$ value of various tyrphostins, these were added in a volume of 0.5 μl (in DMSO; final concentration, 0.5%) 15 min before addition of the growth factors, in a range of concentrations. Phosphorylation was initiated by addition of [γ-$^{32}$P]ATP (5 μl, 3–5 μCi; final concentration, 2 μM) and terminated after 2 min by addition of 10 μl of a solution containing 6% SDS, 30% β-mercaptoethanol, 40% glycerol, and 0.5 mg/ml bromophenol blue. The samples were heated for 5 min at 95° C. and subjected to polyacrylamide gel electrophoresis in the presence of 0.4% SDS, using 10% acrylamide gels. The gels were stained, dried and subjected to autoradiographic analysis. For quantification of radioactivity in electrophoresis gels, a Phospho-Imager (Molecular Dynamics, Fuji, or Bio-Rad) was used according to the instructions of the manufacturers. To obtain autoradiograms, objects were exposed to X-ray film (Fuji RX or KIodak X-OMAT) with intensifying screens at −70° C.

Inhibition of cell proliferation and recovery: Monolayer cell growth inhibition and recovery experiments were repeated 3 or 4 times. Each experiment was performed in triplicate. Approximately 15,000 cells (SMC or EC) in 1 ml of culture medium supplemented with 15% FCS were seeded on day 0 in 15 mm-wells precoated with fibronectin. Cultures were treated with a tyrphostin (10 μM) dissolved in 0.1% DMSO on days 1 and 3. On day 6, cultures were washed and the cells allowed to recover. Typically cells were counted on days 3 and 5 for inhibition, and on days 7, 10 and 15 for recovery, other schedules were also employed as reported below. The medium supplemented with serum (M-199 with ECGS for EC, and DMEM for SMC) was changed every other day throughout the experiment.

Experimental results:

Inhibition of PDGF-induced tyrosine phosphorylation by tyrphostins:

Stimulation of porcine arterial SMC with PDGF-BB (100 ng/ml) resulted in strong phosphorylation of the PDGF β-receptor on tyrosine residues. Addition of AG1295, AG1990, AG1992 or AG1851 to the cells prior to PDGF-stimulation completely inhibited PDGF β-receptor tyrosine-phosphorylation. However, AG1989 and AG1991 did not affect the degree of tyrosine phosphorylation in the cells.

Table 1 below presents IC$_{50}$ values (50% inhibition of phosphorylation, μM) of various tyrphostins with respect to PDGFR, SRC Kinase and EGFR, as was performed on isolated membranes or intact cells expressing these receptors (see experimental methods section above).

TABLE 1

| Compound | PDGFR | SRC kinase | EGFR |
| --- | --- | --- | --- |
| AG1851 | 5 | >30 | >30 |
| AG1990 | 1.0 | 20 | >30 |
| AG1991 | 20 | >30 | >30 |
| AG1992 | 1.0 | >30 | >30 |

Effects of tyrphostins on cell proliferation:

A. Porcine aortic smooth muscle cells (SMC):

Treatment of SMC with AG1295 (10 μM) resulted in a 46% mean reduction in SMC count by day 3 compared to DMSO treated control cells and a 78%±2% (mean±SD) reduction over control by day 5. AG1992 (10 μM) inhibited SMC growth by 87% at days 5, and AG1851 (10 μM) by 79%. AG1990 and AG1989 inhibited SMC growth by 50% and 47%, respectively, whereas AG1991 did not exhibit any inhibitory effect on these cells. As further described below, the inhibitory effect of AG1851, AG1992, AG1295, AG1990 and AG1989 was completely reversible. Table 2 summarizes the maximal inhibition in SMC growth for each tyrphostin relatively to its control.

TABLE 2

| Treatment | mean reduction in SMC count compared to control cells |
| --- | --- |
| AG1295 | 78% |
| AG1992 | 87% |
| AG1851 | 79% |
| AG1990 | 50% |
| AG1989 | 47% |
| AG1991 | 0% |

FIG. 3 presents the maximal inhibitory and recovery effects on porcine arterial SMC growth inflicted by 10 μM of AG1851, AG1992, AG1991, AG1990 and AG1989. Cells were grown in the presence of the specified tyrphostins and were counted after seven days in culture. On day 7 the cultures were washed and the cells allowed to recover. Seven days later they were counted for recovery. The bar graph show the maximal inhibition and the recovery for each tyrphostin employed and for controls. Please note that the inhibitory effect of AG1851, AG1992, AG1990 and AG1989 was completely reversible, whereas AG1991 did not exhibit any inhibitory effect.

Figure 4:
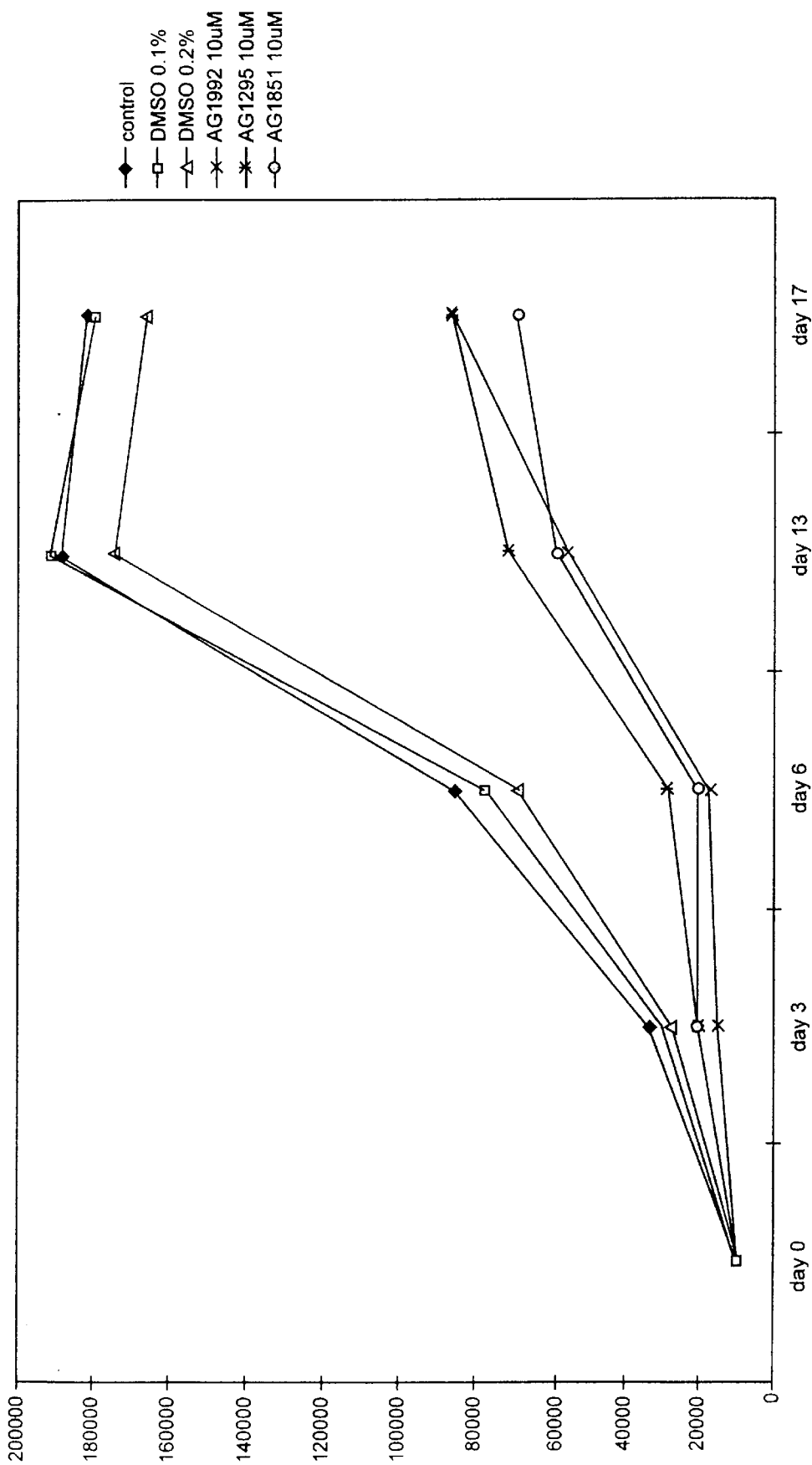
FIG. 4 presents plots demonstrating the inhibitory and recovery effects of tyrphostins on porcine SMC proliferation.

FIG. 4 demonstrates the inhibitory and recovery effects of AG1851, AG1992 and AG1295 on porcine SMC proliferation. Cells were grown in the presence of the specified tyrphostins and were counted on days 3, 6, 13 and 17 in culture. On day 7 the cultures were washed and the cells allowed to recover. All three tyrphostins showed very potent growth inhibition effect as compared with controls. This inhibitory effect was reversible, and the cells resumed normal growth response as soon as the treatment with the tyrphostins was withdrawn.

Figure 5:
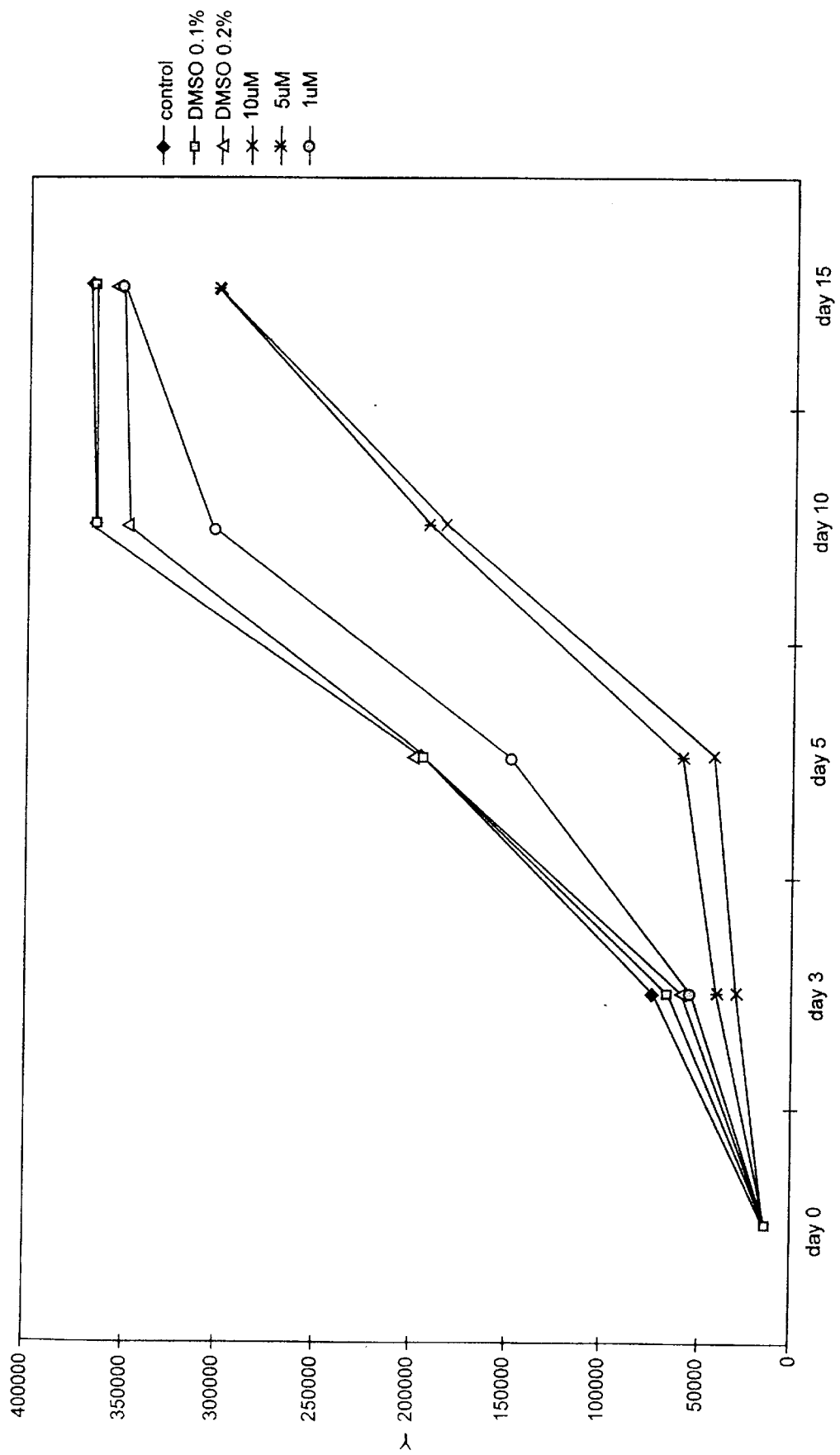
FIG. 5 presents plots demonstrating AG1851 dose response affecting porcine SMC proliferation.

FIGS. 5 demonstrates the results of a dose response experiment for the inhibitory effect and recovery of AG1851 on porcine SMC. Cells were grown in the presence of the specified concentrations of AG1851 and were counted on days 3, 5, 10 and 15 in culture. On day 6 the cultures were washed and the cells allowed to recover. At 10 μM concentration AG1851 had the most effective inhibitory response without having a substantial toxic effect on the cells. As expected from the experiments so far described, normal cell growth appeared immediately after treatment with AG1851 was discontinued.

Figure 6:
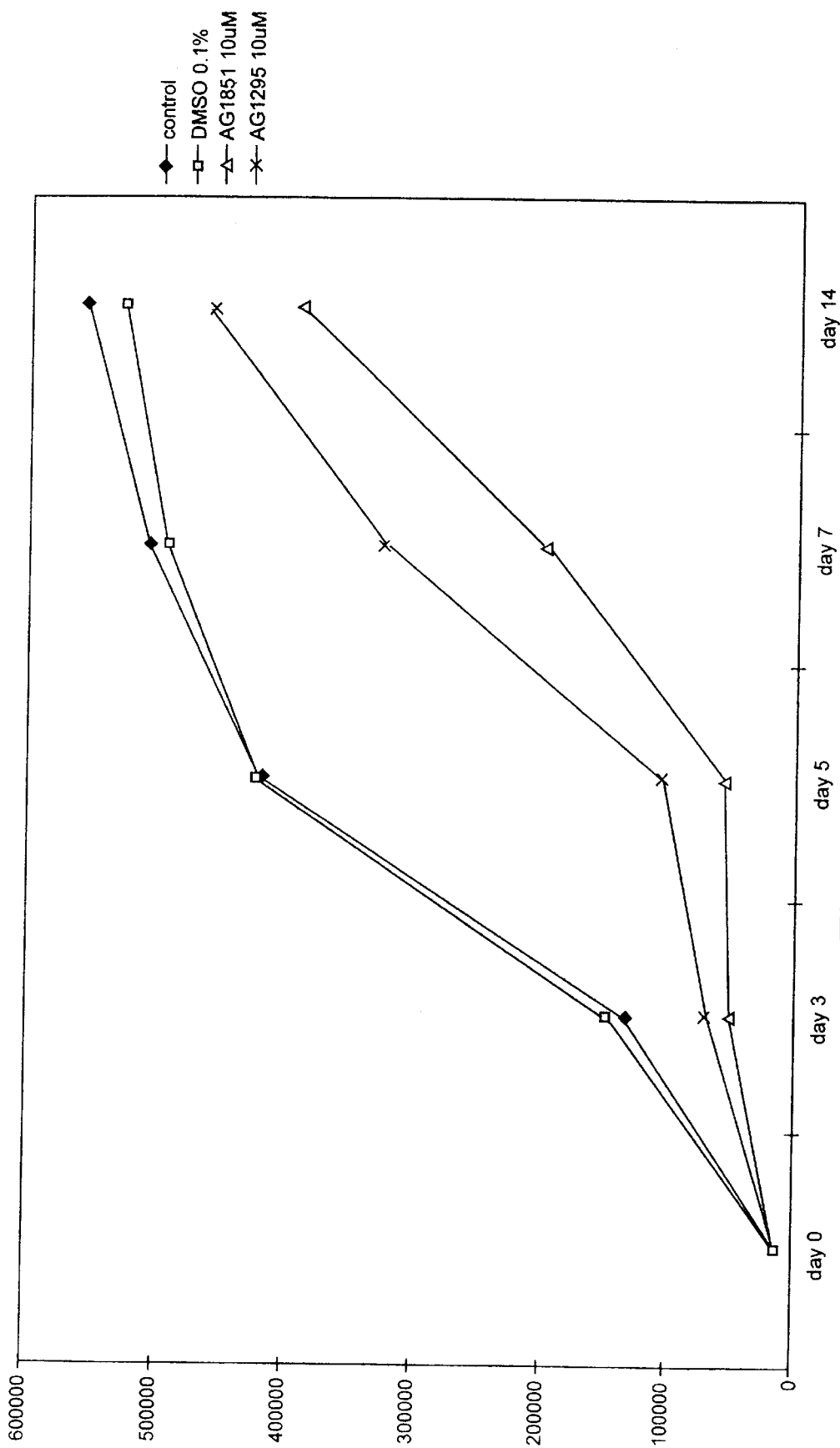
FIG. 6 presents comparative plots demonstrating the inhibitory and recovery effects of AG1851 versus AG1295 on porcine SMC proliferation.

FIG. 6 demonstrates the inhibitory effect and recovery of AG1851 versus AG1295 on porcine SMC. Cells were grown in the presence of 10 μM of the specified tyrphostins and were counted on days 3, 5, 7 and 14 in culture. On day 6 the cultures were washed and the cells allowed to recover. Both tyrphostins are highly effective in blocking proliferation and exhibit low lasting toxicity on SMC growth after removal. The maximal inhibitory effect of AG1851 was 78%, which was higher than the effect of AG1295, 65% in this experiment.

Figure 7:
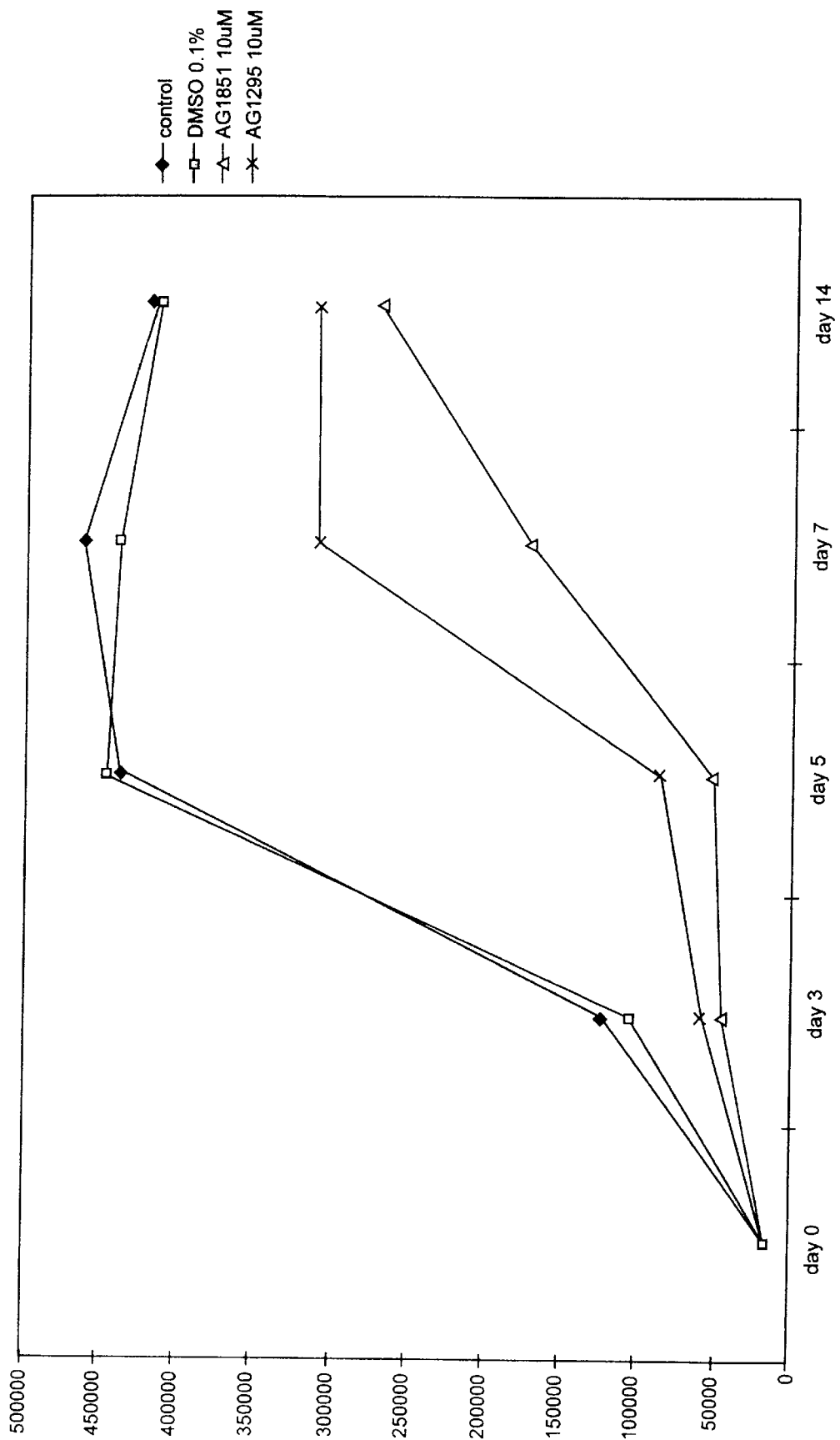
FIG. 7 presents comparative plots demonstrating the inhibitory and recovery effects of AG1992 versus AG1295 on porcine SMC proliferation.

FIG. 7 demonstrates the inhibitory effect and recovery of AG1992 versus AG1295 on porcine SMC. Cells were grown in the presence of 10 μM of the specified tyrphostins and were counted on days 3, 5, 7 and 14 in culture. On day 6 the cultures were washed and the cells allowed to recover. Both tyrphostins are very effective proliferation inhibitors demonstrating low lasting toxicity on SMC growth after removal. The maximal inhibitory effect of AG1992 was 89%, which was higher than the effect of AG1295, 81% in this experiment.

B. Porcine endotlielial cells (EC)

In general, the inhibitory effect of AG1295 on porcine EC proliferation was minimal, resulting in only about a 10% mean reduction of cell growth by day 3, and a 13.5%±3% reduction by day 5, compared to controls. This mild inhibitory effect was completely reversible.

Figure 8:
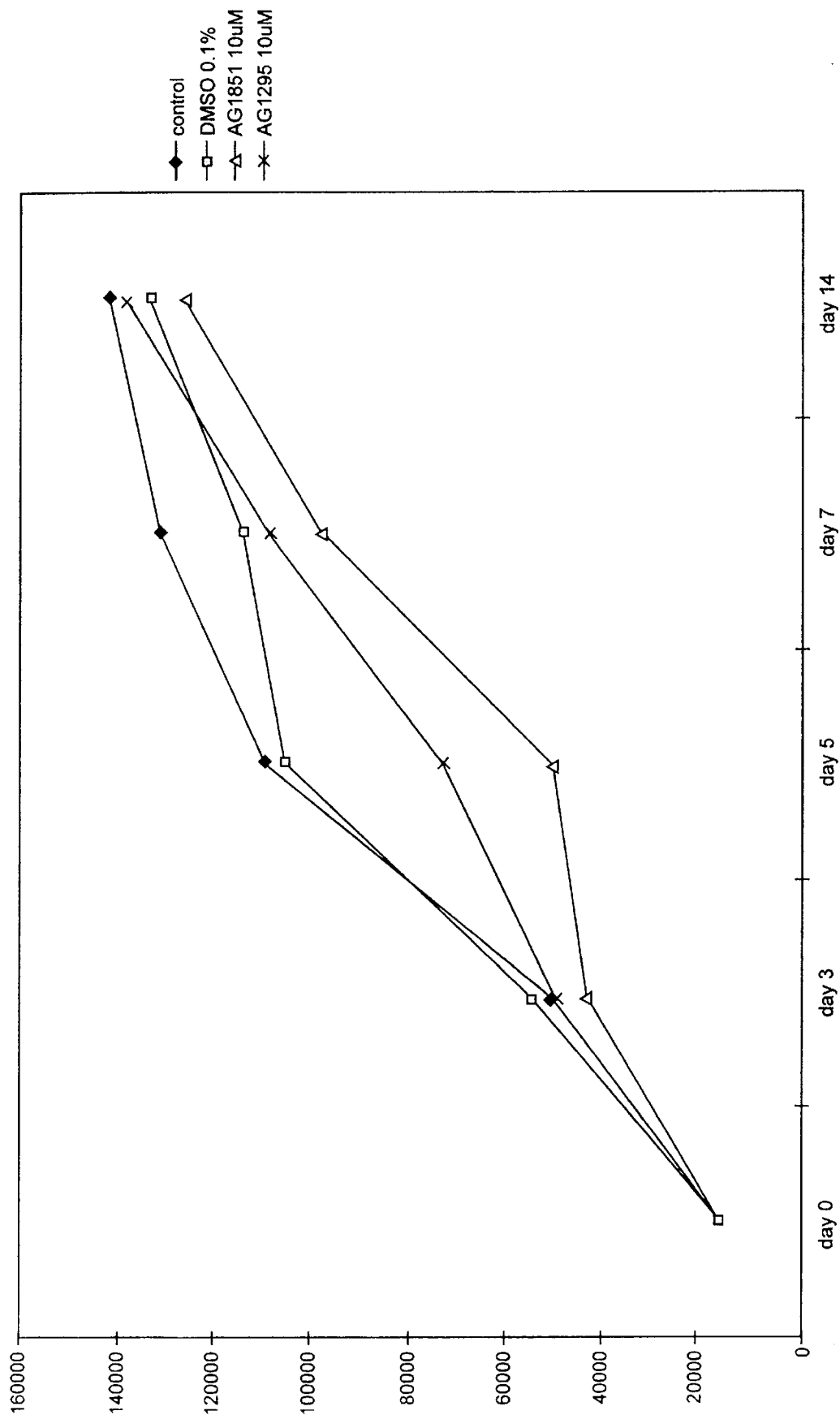
FIG. 8 presents comparative plots demonstrating the inhibitory and recovery effects of AG1992 versus AG1295 on porcine endothelial cell (EC) proliferation.

FIG. 8 demonstrates the inhibitory effect and recovery of AG1992 versus AG1295 on porcine EC. Cells were grown in the presence of 10 μM of the specified tyrphostins and were counted on days 3, 5, 7 and 14 in culture. On day 6 the cultures were washed and the cells allowed to recover. The maximal inhibitory effect of AG1992 was 52%, which was higher than the effect of AG1295, 22% in this experiment.

Figure 9:
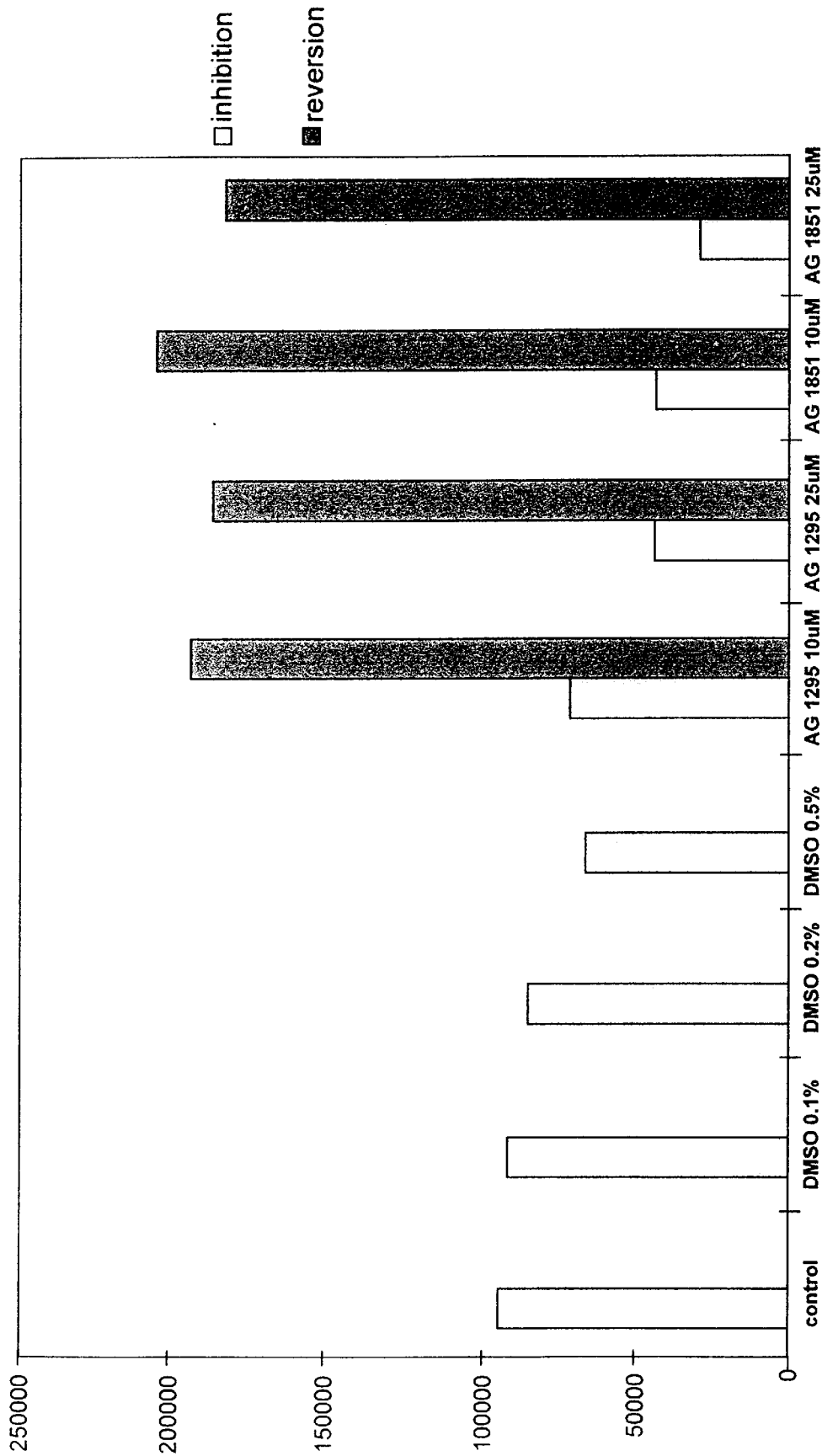
FIG. 9 is a bar graph presenting the maximal inhibitory and recovery effects of varying concentrations of the tyrphostins AG1851 and AG1295 on human internal mammary artery smooth muscle cells (IMA SMC) growth.

C. Human internal mammary artery smooth muscle cells (IMA SMC):

FIG. 9 presents the maximal inhibitory and recovery effects on human IMA SMC growth inflicted by 10 or 25 μM of AG1851 and AG1295. Cells were grown in the presence of the specified tyrphostins and were counted after seven days in culture. On day 7 the cultures were washed and the cells allowed to recover. Seven days later they were counted for recovery. The bar graph show the maximal inhibition and the recovery in each experiment and for controls. Treatment with AG1295 (25 μM) resulted in a 48% mean reduction in IMA SMC proliferation by day 5 compared to untreated or DMSO-treated cells. Treatment with AG1851 (25 μM) resulted in a 54% inhibition of IMA SMC proliferation. These effects were completely reversible upon removal of the tyrphostin.

A pharmaceutical composition of and method for in vitro tyrphostins delivery:

According to the present invention tyrphostins are delivered to a balloon treated area of an artery by coating the balloon with tyrphostin slow release nanoparticles which slowly discharge the tyrphostin at the balloon treated area, thereby cell proliferation at the treated area is inhibited.

To this end a tyrphostin compound was formulated in nanoparticles for example, poly lactic acid (PLA) nanoparticles loaded with tyrphostin prepared by an oil-in-water (O/W) emulsification/solvent evaporation method as follows.

Fifty mg PLA and 3 mg of the selected tyrphostin(s) were dissolved in an organic mixture of 0.5 ml dichloromethane and 10 ml acetone. The organic solution was added to 20 ml of an aqueous solution containing 0.5% Poloxamer F68. The oil-in-water (O/W)-type emulsion was stirred by means of a magnetic stirrer at 20 W power output for 5 min. The organic solvents were evaporated in a rotating evaporator at pressure of 20 mm Hg, giving a colloidal suspension of nanoparticles. Finally, the obtained suspension was passed through a Whatman 40 filter paper.

Yield was 6 ml containing 600 μg of the tyrphostin (100 μg/ml). Particle size was 110–130 nm.

This formulation may be employed for inhibiting cell proliferation via slow release mechanism in various proliferative disorders, including, but not limited to, psoriasis, papilloma, restenosis, atherosclerosis, in-stent stenosis, vascular graft restinosis, pulmonary fibrosis, glomerular nephritis, rheumatoid arthritis and PDGF receptor associated malignancies.

While the invention has been described with respect to a limited number of embodiments, it will be appreciated that many variations, modifications and other applications of the invention may be made.

LIST OF REFERENCES CITED

1. Ross, R. Platelet-derived growth factor. Lancet, 1: 1179–1182, 1989.

2. Heldin, C. H. Structural and functional studies on platelet-derived growth factor. EMBO J., 11: 4251–4259, 1992.

3. Yarden, Y., Escobedo, J. A., Kuang, W-J., Yang-Feng, T. L., Daniel, T. O., Tremble, P. M., Chen, E. Y., Ando, M. E., Harkins, R. N., Francke, U., Friend, V. A., Ullrich, A., Williams, L. T. Structure of the receptor for platelet-derived growth factor helps define a family of closely related growth factor receptors. Nature (Lond.), 323: 226–232,1986.

4. Matsui, T., Heidaran, M., Miki, T., Popescu, N., LaRochelle, W., Kraus, M., Pierce, J., and Aatonson, S. Isolation of a novel receptor cDNA establishes the existence of two PDGF receptor genes. Science (Washington DC), 243: 800–804, 1989.

5. Claesson-Welsh, L., Eriksson, A., Westermark, B., and Heldin, C-H. cDNA cloning and expression of the human A-type platelet-derived growth factor (PDGF) receptor establishes structural similarity to the B-type PDGF receptor. Proc. Natl. Acad. Sci. USA, 86: 4917–4921, 1989.

6. Escobedo, J. A., Barr, P. J., and Williams, L. T. Role of tyrosine kinase and membrane-spanning domains in signal transduction by platelet-derived growth factor receptor. Mol. Cell. Biol., 8: 5126–5131, 1988.

7. Ross, R. Mechanisms of atherosclerosis-a review. Adv. Nephrol. Necker Hosp., 19: 79–86, 1990.

8. Ross, R. The pathogenesis of atherosclerosis: a perspective for the 1990s. Nature (Lond.) 362: 801–809, 1993.

9. Shaw, R. J., Benedict, 5. H., Clark, R. A., and King, T. E. Pathogenesis of pulmonary fibrosis in interstitial lung disease. Alveolar macrophage PDGF(B) genie activation and up-regulation by interferon -γ. Am. Rev. Respir. Dis., 143: 167–173, 1991.

10. Gesualdo, L., Ranierei, E., Pannarale, G., Di Paolo, S., and Schena, F. P. Platelet derived growth factor and proliferative glomerulonephritis. Kidney Int., 43 (Suppl. 39): 86 89, 1993.

11. Rubin, K., Terracio, L., Ronnstrand, L., Heldin, C. H., and Klareskog, L. Expression of platelet-derived growth factor receptors is induced on connective tissue cells during chronic synovial inflammation. Scand. J. Immunol., 27:285–294. 1988.

12. Waterfield, M. D., Scrace, G. T., Whittle, N., Stroobant, P., Johnson, A., Wasteson, A., Westermark, B., Heldin, C. H., Huang, J. S., and Deuel, T, F. Platelet-derived growth factor is structurally related to the putative transforming protein p28 sis of simian sarcoma virus. Nature (Lond.), 304: 35–39, 1983.

13. Doolittle, R. F., Hunkapiller, M. W., Hood, L. E., Devare S. G., Robbins, K. C., Aaronson, S. A., and Antoniades, H. N. Simian sarcoma virus oncogene, v-sis, is derived from the gene (or genes) encoding a platelet-derived growth factor. Science (Washington DC), 221: 275–277, 1983.

14. Heldin, C-H., and Westermark, B. Platelet-derived growth factor and autocrine mechanisms of oncogenic processes. CRC Crit. Rev. Oncog., 2: 109–124, 1991.

15. Engstrom, U., Engstrom, A., Ernlund, A., Westermark, B., and Heldin, C-H. Identification of a peptide antagonist for platelet-derived growth factor. J. Biol. Chem., 267: 16581–16587,1992.

16. Vassbotn, F. S., Andersson, M., Westermark, B., Heldin, C. H., and Ostman, A. Reversion of autocrine transformation by a dominant negative platelet-derived growth factor mutant. Mol. Cell. Biol., 13: 4066–4076. 1993.

17. Shamah, S. M., Stiles, C. D., and Guha, A. Dominant-negative mutants of platelet derived growth factor revert the transformed phenotype of human astrocytoma cells. Mol. Cell. Biol., 13: 7203–7212, 1993.

18. Ueno, H.. Colbert, H., Escobedo, J. A., and Williams, L. T. Inhibition of PDGFR receptor signal transduction by coexpression of a truncated receptor. Science (Washington DC), 252: 844–848, 1991.

19. Levitzki, A. Tyrphostins: tyrosine kinase blockers as novel antiproliferative agents and dissectors of signal transduction. FASEB J., 6: 3275–3282, 1992.

20. Bilder, G. E., Krawiec, J. A., McVety, K., Gazit, A., Gilon, C., Lyall, R., Zilberstein A., Levitzki, A., Perrone, M. H., and Schreiber, A. B. Tyrphostins inhibit PDGF induced DNA synthesis acid associated early events in smooth muscle cells. Am. J. Physiol., 260: C721–C730, 1991.

21. Bryckaert, M. C., Eldor, A., Fontanay, M., Gazit, A., Osherov, N., Gilon, C., Levitzki, A., and Tobelem, G. Inhibition of platelet-derived growth factor-induced nutogenesis and tyrosine kinase activity in cultured bone marrow fibroblasts by tyrphostins. Exp. Cell. Res., 199: 255–261, 1992.

22. Kovalenko, M., Gazit, A., Bohmer, A., Rorsman, C., Ronnstrand, L., Heldin, C. H., Waltenberger J., Bohmer F. D., and Levitzki A. Selective platelet-derived growth factor receptor kinase blockers reverse sis-transformation. Cancer Research, 54:6106–6114.

23. Kovalenko, M., Ronnstrand, L., Heldin, C. H., Loubtchekov, M., Gazit, A. Levitzki, A., and Bohner F. D. Phosphorylation site-specific inhibition of platelet derived growth factor β-receptor autophosphorylation by the receptor blocking tryphostin AG1296. Biochemistry, 36:6260–6269.

24. Golomb, G., Fishbein, I., Banai, S., Mishaly, D., Moscovitz. D., S.

Gertz, D., Gazit, A,., Levitzki, A. Controlled delivery of a tyrphostin inhibits intimal hyperplasia in a rat carotid artery injury model. Artherosclerosis, 125:171–182, 1996.

25. Sirois, M. G., Simms, M., Edelman, E. R. Antisense oligonucleotide inhibition of PDGF-β subunit expression directs suppression of intimal thickening. Circulation, 95:669–676, 1977.

26. Eriksson, A., Siegbahn, A., Westerinark, B., Heldin, C. H., and Claesson-Welsh, L. PDGF α- and β-receptors activate unique and common signal transduction pathways. EMBO J., 11: 543–550, 1992.

What is claimed is:

1. A compound comprising a tyrphostin of the general formula:

wherein R1 and R2 are each independently selected from the group consisting of

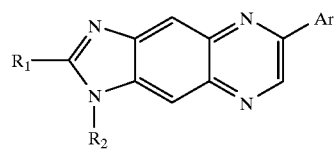

alkyl, alkoxy, halogen, nitro and amine group and Ar is selected from the group consisting of phenyl, ferrocene, thiophene, furane, pyrrole, indole, thiazole, imidazole and pyridine.

2. A compound comprising a tyrphostin selected from the group consisting of:

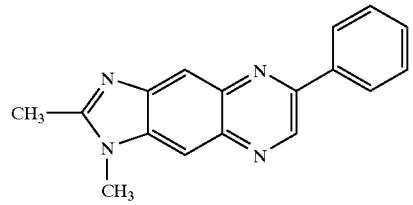

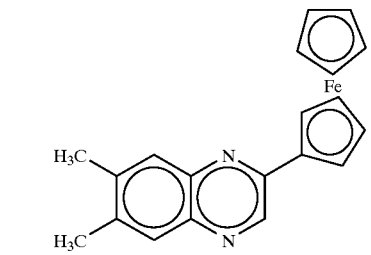

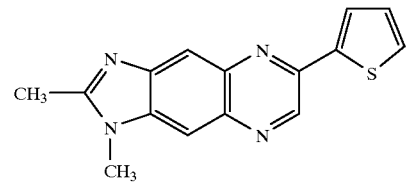

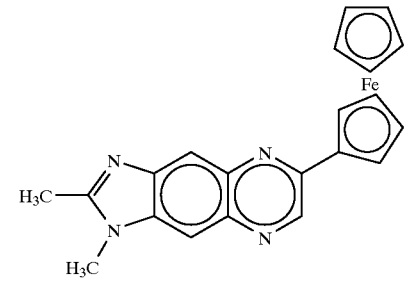

3. A method of inhibiting cell proliferation comprising the step of subjecting the cells to a tyrphostin compound selected from the group consisting of:

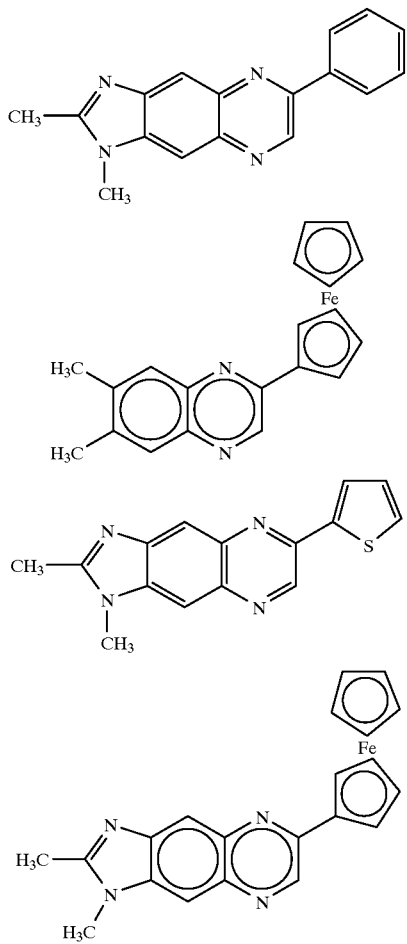

4. The method of claim 3, wherein said cells are of an organism, subjecting the cells to said tyrphostin compound is effected in vivo.

5. The method of claim 4, wherein said organism is a human being.

6. The method of claim 3, wherein subjecting the cells to said tyrphostin compound is effected in vitro.

7. A method of inhibiting cell proliferation comprising the step of subjecting the cells to a tyrphostin compound of the general formula:

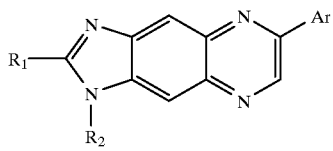

wherein R1 and R2 are each independently selected from the group consisting of alkyl, alkoxy, halogen, nitro and amine group, and Ar is selected from the group consisting of phenyl, ferrocene, thiophene, furane, pyrrole, indole, thiazole, imidazole and pyridine.

8. A pharmaceutical composition for slow release of tyrphostins comprising particles including a slow release carrier and a tyrphostin compound of the general formula:

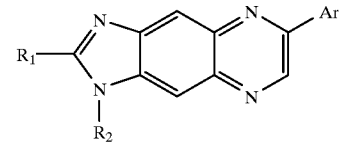

wherein R1 and R2 are each independently selected from the group consisting of alkyl, alkoxy, halogen, nitro and amine group, and Ar is selected from the group consisting of phenyl, ferrocene, thiophene, furane, pyrrole, indole, thiazole, imidazole and pyridine.

9. A method of treating a proliferative disorder of an organism, comprising the step of applying the pharmaceutical composition of claim 8 to said organism.

10. The method of claim 9, wherein said organism is a human being.

11. A method of locally treating a proliferative disorder of a tissue of an organism comprising the step of locally applying the pharmaceutical composition of claim 8 onto said tissue.

12. The method of claim 11, wherein said tissue is an artery.

13. The method of claim 9, wherein said proliferative disorder is selected from the group consisting of psoriasis, papilloma, restenosis, atherosclerosis, in-stent stenosis, vascular graft restinosis, pulmonary fibrosis, glomerular nephritis, rheumatoid arthritis and PDGF receptor associated malignancies.

14. A method of preparing a pharmaceutical composition for slow release of a tyrphostin compound of the general formula:

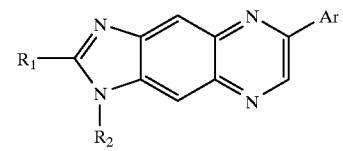

wherein R1 and R2 are each independently selected from the group consisting of alkyl, alkoxy, halogen, nitro and amine group and Ar is selected from the group consisting of phenyl, ferrocene, thiophene, furane, pyrrole, indole, thiazole, imidazole and pyridine; the method comprising the steps of:

(a) dissolving or dispersing a slow release carrier and said tyrphostin compound in an organic solvent for obtaining an organic solution containing said carrier and said tyrphostin compound;

(b) adding said organic solution into an aqueous solution for obtaining an oil-in-water-type emulsion; and (c) evaporating said organic solvent from said oil-in-water-type emulsion for obtaining a colloidal suspension of particles containing said slow release carrier and said tyrphostin compound.

15. The method of claim 14, wherein said slow release carrier is poly lactic acid.

* * * * *